(12) United States Patent
Saito

(10) Patent No.: US 7,951,964 B2
(45) Date of Patent: May 31, 2011

(54) FLUORINE-CONTAINING BORONIC ACID ESTER COMPOUND AND METHOD FOR PRODUCING THE SAME

(75) Inventor: Satoru Saito, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 12/988,670

(22) PCT Filed: Apr. 21, 2009

(86) PCT No.: PCT/JP2009/057893
§ 371 (c)(1),
(2), (4) Date: Oct. 20, 2010

(87) PCT Pub. No.: WO2009/131107
PCT Pub. Date: Oct. 29, 2009

(65) Prior Publication Data
US 2011/0040118 A1    Feb. 17, 2011

(30) Foreign Application Priority Data
Apr. 22, 2008    (JP) ................................ 2008-110865

(51) Int. Cl.
*C07D 307/04* (2006.01)
(52) U.S. Cl. ..................................................... 549/213
(58) Field of Classification Search .................. 549/213
See application file for complete search history.

(56) References Cited

U.S. PATENT DOCUMENTS
7,195,719 B1    3/2007    Wand et al.

FOREIGN PATENT DOCUMENTS
WO    WO 02/18514 A1    3/2002
WO    WO 02/44189 A1    6/2002
WO    WO 03/040074 A1    5/2003

OTHER PUBLICATIONS

International Search Report from corresponding PCT application No. PCT/JP2009-057893, dated May 26, 2009.
Johansson, G, et al., "Fluorophobic Effect in the Self-Assembly of Polymers and Model Compounds Containing Tapered Groups into Supramolecular Columns", *Macromolecules*, vol. 29, No. 2, 1996, pp. 646-660.
Miyaura, Norio et al., "Palladium-Catalyzed Cross-Coupling Reactions of Organoboron Compounds", *Chemical Reviews*,vol. 95, No. 7, 1995, pp. 2457-2483.
Morgan, Alexander B, et al., "Synthesis, Flame-Retardancy Testing, and Preliminary Mechanism Studies of Nonhalogenated Aromatic Boronic Acids: A New Class of Condensed-Phase Polymer Flame-Retardant Additives for Acrylonitrile-Butadiene-Styrene and Polycarbonate", *Journal of Applied Polymer Science*, vol. 76, 2000, pp. 1257-1268.

*Primary Examiner* — Susannah Chung
*Assistant Examiner* — Samantha L Shterengarts
(74) *Attorney, Agent, or Firm* — Brinks Hofer Gilson & Lionie

(57)    ABSTRACT

A fluorine-containing boronic acid ester compound

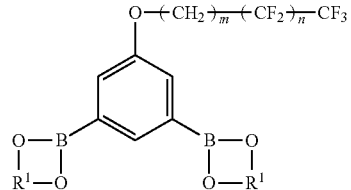

($R^1$: a linear or branched divalent aliphatic hydrocarbon group having 2 to 10 carbon atom, m: 1 to 5, and n: 3 to 7) having a low melting point is produced by reacting a 3,5-dihalogeno fluorine-containing phenol derivative

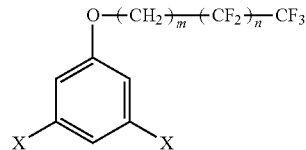

with a dialkoxyborane

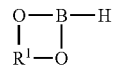

The fluorine-containing boronic acid ester compound is highly soluble in organic solvents and has a low melting point. The fluorine-containing boronic acid ester compound can suitably be used as a starting material for the production of conjugated polymer materials or as a curing agent for elastomeric polymer materials.

6 Claims, No Drawings

FLUORINE-CONTAINING BORONIC ACID ESTER COMPOUND AND METHOD FOR PRODUCING THE SAME

RELATED APPLICATION

This application is a 35 U.S.C. §371 national phase filing of International Patent Application No. PCT/JP2009/057893, filed Apr. 21, 2009, through which and to which priority is claimed under 35 U.S.C. §119 to Japanese Patent Application No. 2008-110865, filed Apr. 22, 2008.

TECHNICAL FIELD

The present invention relates to a fluorine-containing boronic acid ester compound and a method for producing the same. More specifically, the present invention relates to an aromatic fluorine-containing boronic acid ester compound having an improved solubility in organic solvents and having a low melting point, and a method for producing the same.

BACKGROUND ART

Organic boronic acids or ester compounds thereof are stable in water and air, and are utilized in cross-coupling reactions using a transition metal complex as a catalyst. Particularly, the reaction using a palladium compound as a catalyst is known as the Suzuki-Miyaura reaction, which is industrially used in pharmaceutical synthesis, agricultural chemicals pesticide synthesis, liquid crystal material synthesis, etc. (see Non-Patent Document 1).

Moreover, recently, aromatic diboronic acids or ester compounds thereof are heavily used in the investigation study of OLED (organic EL) and conductive polymer materials. However, it is difficult to purify aromatic diboronic acids because many of them contain boroxine as an impurity. There is another drawback that aromatic diboronic acids are converted into boroxine by heating, thereby reducing the reactivity. In contrast, it is easy to purify aromatic diboronic acid ester compounds; however, many of them are poorly soluble in organic solvents and have a very high melting point.

PRIOR ART DOCUMENTS

Non-Patent Documents

Non-Patent Document 1: Chem. Rev., Vol. 95, pp. 2457 (1995)

Non-Patent Document 2: J. Appl. Poly. Sci., Vol. 76, pp. 1257 (2000)

Non-Patent Document 3: Macromolecules, Vol. 29, pp. 646 (1996)

OUTLINE OF THE INVENTION

Problem to be Solved by the Invention

An object of the present invention is to provide an aromatic fluorine-containing diboronic acid ester compound having an improved solubility in organic solvents and having a low melting point, and a method for producing the same.

Means for Solving the Problem

The present invention provides a fluorine-containing boronic acid ester compound represented by the general formula:

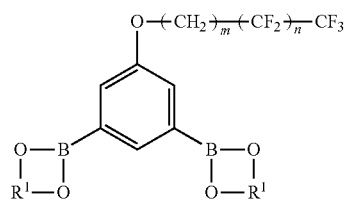

wherein $R^1$ is a linear or branched divalent aliphatic hydrocarbon group having 2 to 10 carbon atoms, m is an integer of 1 to 5, and n is an integer of 3 to 7. The fluorine-containing boronic acid ester compound is produced by the reaction of a 3,5-dihalogeno fluorine-containing phenol derivative represented by the general formula:

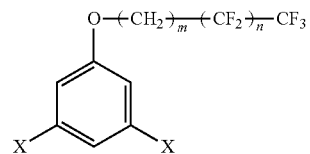

with a dialkoxyborane represented by the general formula:

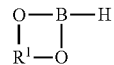

EFFECT OF THE INVENTION

The fluorine-containing boronic acid ester compound of the present invention is highly soluble in organic solvents and has a low melting point. The fluorine-containing boronic acid ester compound can suitably be used as a starting material for the production of conjugated polymer materials or as a curing agent of elastomeric polymer materials.

EMBODIMENT FOR CARRYING OUT THE INVENTION

The fluorine-containing boronic acid ester compound of the present invention is represented by the general formula:

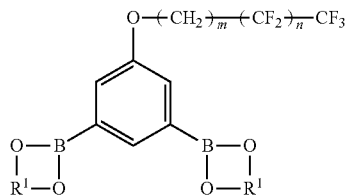

In the fluorine-containing boronic acid ester compound, $R^1$ is a linear or branched divalent aliphatic hydrocarbon group having 2 to 10 carbon atoms. Examples of $R^1$ include —CH$_2$C(CH$_3$)$_2$CH$_2$—, —CH$_2$CH$_2$CH$_2$—, —C(CH$_3$)$_2$C(CH$_3$)$_2$—, —C(CH$_3$)$_2$CH$_2$C(CH$_3$)$_2$—, and the like; particularly, —C(CH$_3$)$_2$C(CH$_3$)$_2$— is selected in terms of ease of production. m is an integer of 1 to 5, and preferably 1 to 3 particularly when resistance to heat is required. n is an integer of 3 to 7, and preferably 3 to 5.

Specific examples of the fluorine-containing boronic acid ester compound include those shown below.

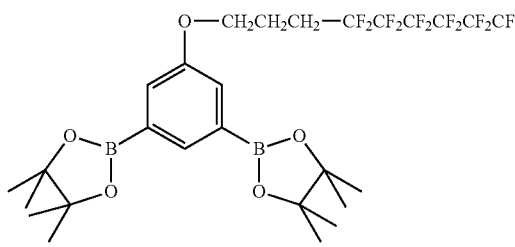

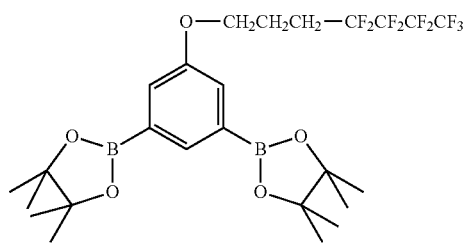

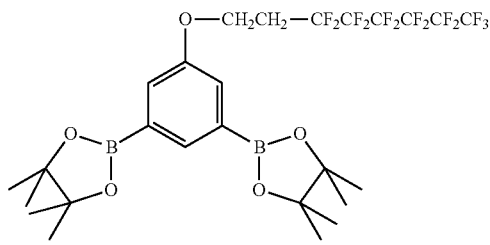

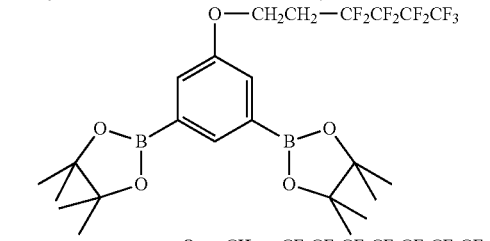

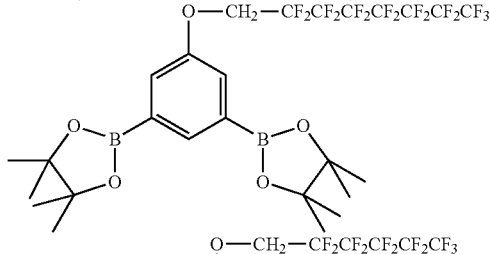

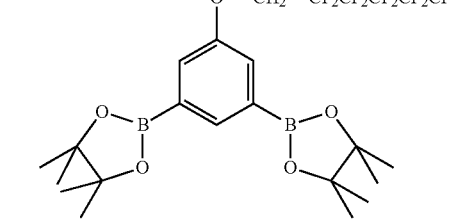

These fluorine-containing boronic acid ester compounds can be produced, for example, by the following process.

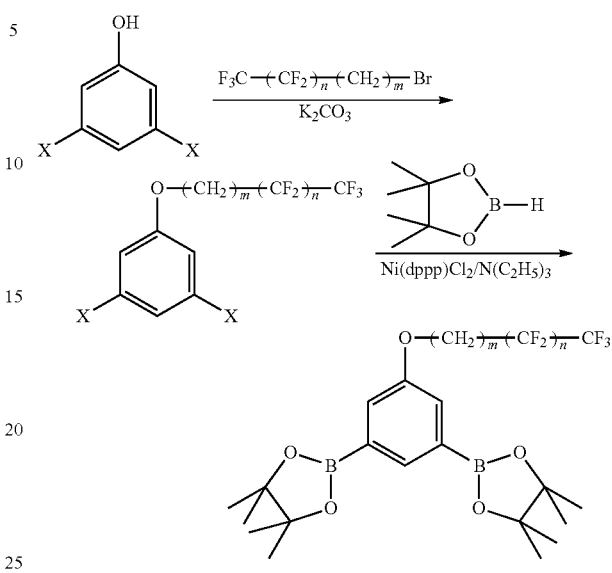

Note: Ni(dppp)Cl$_2$: [1,3-bis(diphenylphosphino)propane]dichloronickel

The reaction of the second step in the above process is carried out by reacting a 3,5-dihalogeno fluorine-containing phenol derivative with a dialkoxyborane using a Group-10 transition metal catalyst. In the 3,5-dihalogeno fluorine-containing phenol derivative, X is a halogen atom, preferably a bromine or iodine atom, and particularly a bromine atom is more preferable. Examples of usable dialkoxyboranes include 4,4,5,5-tetramethyl-1,3,2-dioxaborolane(pinacolborane), 4,4,6-trimethyl-1,3,2-dioxaborinane, 5,5-dimethyl-1,3,2-dioxaborinane, 1,3,2-dioxaborinane, and the like. In consideration of the chemical stability of the produced boronic acid ester, 4,4,5,5-tetramethyl-1,3,2-dioxaborolane(pinacolborane) is preferred.

As the Group-10 transition metal catalyst used in the reaction, a nickel or palladium catalyst can be used. Examples of nickel catalysts include [1,2-bis(diphenylphosphino)ethane]dichloronickel, [1,3-bis(diphenylphosphino)propane]dichloronickel, [1,4-bis(diphenylphosphino)butane]dichloronickel, [1,1'-bis(diphenylphosphino)ferrocene]dichloronickel, bis(triphenylphosphine)dichloronickel, and the like. Examples of palladium catalysts include bis(dibenzylideneacetone)palladium, [1,1'-bis(diphenylphosphino)ferrocene]dichloropalladium, tetrakis(triphenylphosphine)palladium, palladium acetate, and the like. A suitable catalyst is a nickel catalyst, and particularly [1,3-bis(diphenylphosphino)propane]dichloronickel is preferable.

Such a catalyst is used at a ratio of 0.1 to 20 mol %, and preferably 1 to 10 mol %, with respect to the 3,5-dihalogeno fluorine-containing phenol derivative.

In this reaction, hydrogen halide is produced as a by-product, and it is therefore necessary to add a base in an amount of stoichiometry or more as a scavenger. Examples of bases include organic acid alkali metal salts, such as potassium acetate and potassium phenolate, inorganic acid alkali metal salts, such as potassium phosphate and potassium carbonate, and tertiary amines, such as triethylamine and diisopropylethylamine; among these, tertiary amines are preferred because the side reaction is suppressed, and triethylamine is particularly preferred.

The reaction is carried out in a toluene solvent under an inert gas (e.g., nitrogen) atmosphere at about 80 to 110° C. for about 6 to 48 hours (see Non-Patent Documents 2 and 3).

The fluorine-containing boronic acid ester compounds can be reacted with, for example, dihalogenated benzene to synthesize polyphenylene, which is a conjugated polymer material.

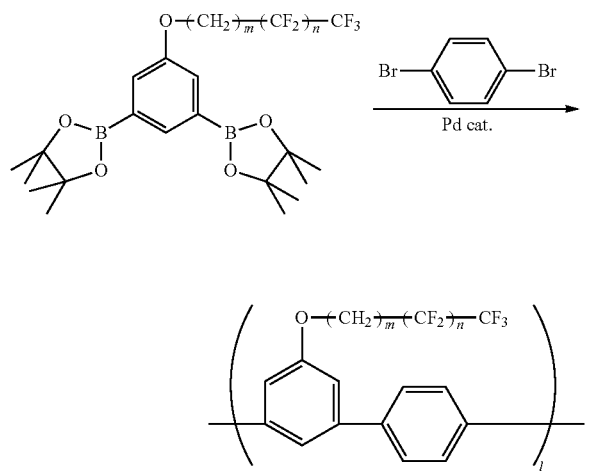

Moreover, the fluorine-containing boronic acid ester compound of the present invention can suitably be used as a curing agent of elastomeric polymer materials. The elastomeric cured products obtained therefrom are excellent in chemical resistance, heat resistance, and low-temperature characteristics, and can effectively be used in the automobile industry, semiconductor production industry, aircraft industry, etc.

EXAMPLES

The following describes the present invention with reference to examples.

Reference Example 1

Production of Reaction Starting Material

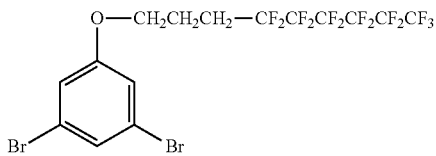

In a nitrogen atmosphere at 65° C., 10 g (40 mmol) of 3,5-dibromophenol was added to a dimethylformamide (150 ml) solution containing 13.5 g (98 mmol) of potassium carbonate. Subsequently, 19.5 g (44 mmol) of 1H,1H,2H,2H,3H,3H-perfluorononyl bromide was added dropwise, followed by reaction for 2 hours. After the completion of the reaction, an usual reaction treatment was carried out, and the resulting crude product was recrystallized with ethanol, thereby obtaining 16.7 g (yield based on 3,5-dibromophenol: 68%) of 3,5-dibromo-1-(1H,1H,2H,2H,3H,3H-perfluorononane-1-yloxy)benzene as a slightly reddish scale-like crystal.

Example

Production of Fluorine-Containing Boronic Acid Ester Compound

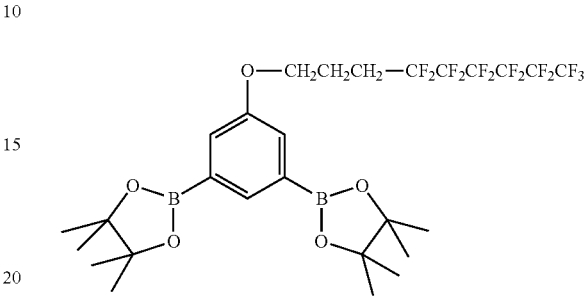

To a toluene (130 ml) solution containing 8.0 g (13 mmol) of 3,5-dibromo-1-(1H,1H,2H,2H,3H,3H-perfluorononane-1-yloxy)benzene, 0.35 g (0.65 mmol) of [1,3-bis(diphenylphosphino)propane]dichloronickel, and 7.9 g (78 mmol) of triethylamine, 5.5 g (43 mmol) of 4,4,5,5-tetramethyl-1,3,2-dioxaborolane was added dropwise at a temperature of 80° C. Subsequently, the temperature was raised to 100° C., and the mixture was reacted in a nitrogen atmosphere for 48 hours. The reaction mixture was cooled to room temperature, and then added to a saturated ammonium chloride solution to terminate the reaction. An usual reaction treatment was carried out, and 10.1 g of crude product was obtained as a dark brown solid. The crude product was recrystallized with ethanol, thereby obtaining 7.4 g (yield based on 3,5-dibromo-1-(1H,1H,2H,2H,3H,3H-perfluorononane-1-yloxy)benzene: 80%) of target 1-(1H,1H,2H,2H,3H,3H-perfluorononane-1-yloxy)-3,5-bis-(4,4,5,5-tetramethyl-1,3,2-dioxaborolan-2-yl)benzene as a colorless scale-like crystal.

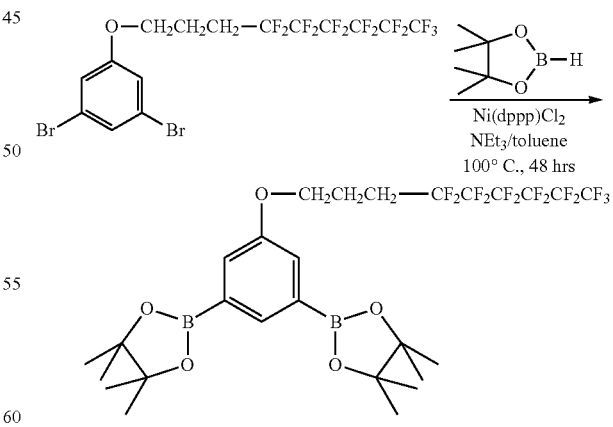

Melting point: 132 to 133° C.

IR (KBr): 2,982 cm$^{-1}$, 1,603 cm$^{-1}$, 1,457 cm$^{-1}$, 1,236 cm$^{-1}$

The following shows the chemical shifts of $^{19}$F-NMR (chemical shift: CFCl$_3$ basis) and $^1$H-NMR (chemical shift: TMS basis) measured in CDCl$_3$:

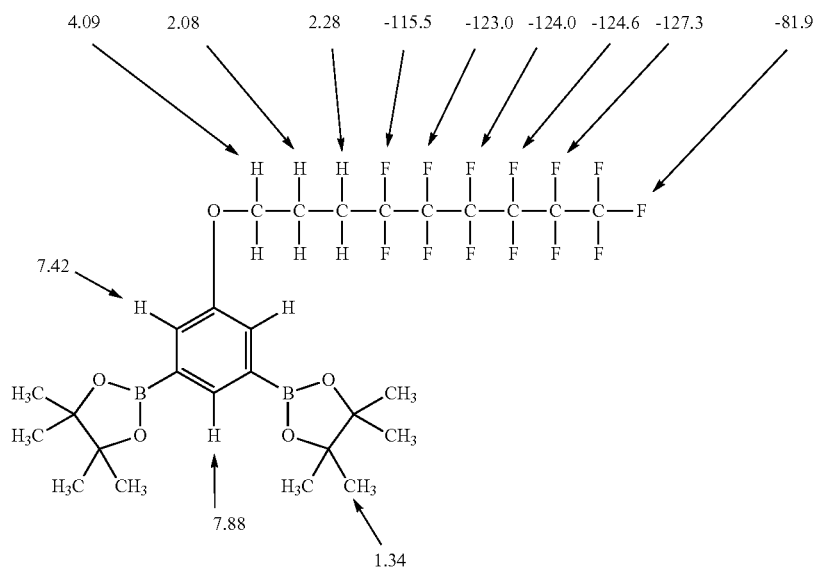

The solubility of the above fluorine-containing boronic acid ester compound in 1,3-bis(trifluoromethyl)benzene, which was a fluorine-containing organic solvent used in the reference example described later, was 5.0 g/10 ml solvent.

Here, the solubility was determined in such a manner that the compound was added and stirred in 10 ml of said fluorine-containing organic solvent at 25° C., and then the maximum amount of addition sufficient to make the solution homogeneous was visually measured.

In contrast, the solubility of 1,4-bis(4,4,5,5-tetramethyl-1,3,2-dioxaborolan-2-yl)benzene (melting point: 240° C.), which was an aromatic diboronic acid ester compound, in said fluorine-containing organic solvent was 0.17 g/10 ml solvent, and 1,4-benzene diboronic acid (melting point: 300° C. or more), which was an aromatic diboronic acid, was insoluble in the fluorine-containing organic solvent.

Furthermore, the solubility of 1,3,5-tris(4,4,5,5-tetramethyl-1,3,2-dioxaborolan-2-yl)benzene (melting point: 200° C. or more), which was an aromatic triboronic acid ester compound, in said fluorine-containing organic solvent was 0.20 g/10 ml solvent.

Reference Example

A Fluorine-Containing Polyether Compound of the Following Formula (100 Parts by Weight; 1+m=102, Viscosity (25° C.): 15 Pa·s)

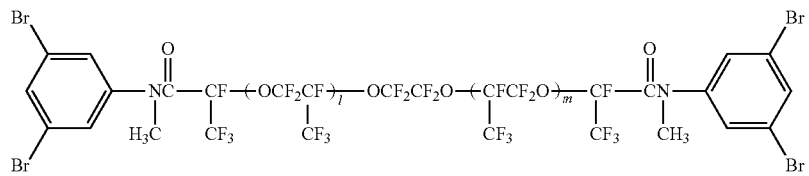

8.0 parts by weight of the 1-(1H,1H,2H,2H,3H,3H-perfluorononane-1-yloxy)-3,5-bis-(4,4,5,5-tetramethyl-1,3,2-dioxaborolan-2-yl)benzene prepared in the example, 0.008 parts by weight of palladium acetate, 0.018 parts by weight of triphenylphosphine, and 9.7 parts by weight of potassium phosphate were added to a mixed solvents containing 125 parts by weight of ethanol, 25 parts by weight of water, and 400 parts by weight of 1,3-bis(trifluoromethyl)benzene. The mixture was mixed under a nitrogen atmosphere at room temperature for 5 minutes, and under reduced pressure, a volatile substance was removed at room temperature. To this mixture, 13 parts by weight of acetylene carbon black was added. As for the curable composition obtained in this manner, the hardening behavior was measured at 130° C. for 30 minutes using a Monsanto disk rheometer.

ML 0.3 dN·m
MH 9.9 dN·m
t10 0.6 minutes
t50 1.2 minutes
t90 14.6 minutes

What is claimed is:

1. A fluorine-containing boronic acid ester compound represented by the general formula:

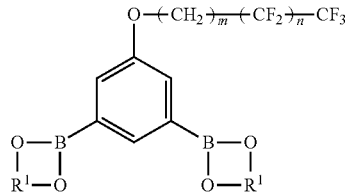

wherein $R^1$ is a linear or branched divalent aliphatic hydrocarbon group having 2 to 10 carbon atoms, m is an integer of 1 to 5, and n is an integer of 3 to 7.

2. The fluorine-containing boronic acid ester compound according to claim 1, wherein $R^1$ is —C(CH$_3$)$_2$C(CH$_3$)$_2$—.

3. A method for producing a fluorine-containing boronic acid ester compound according to claim 1, the method comprising reacting a 3,5-dihalogeno fluorine-containing phenol derivative represented by the general formula:

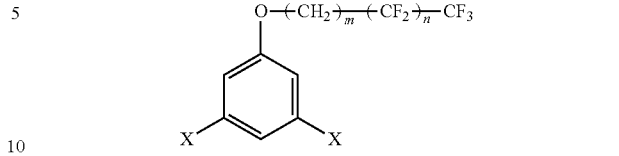

wherein X is a halogen atom, m is an integer of 1 to 5, and n is an integer of 3 to 7, with a dialkoxyborane represented by the general formula:

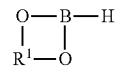

wherein $R^1$ is a linear or branched divalent aliphatic hydrocarbon group having 2 to 10 carbon atoms.

4. The method according to claim 3, wherein the reaction is carried out in the presence of a tertiary amine using a nickel catalyst.

5. The method according to claim 3, wherein $R^1$ is —C(CH$_3$)$_2$C(CH$_3$)$_2$—.

6. The method according to claim 3, wherein each X is Br.

* * * * *